United States Patent [19]
Ogino

[11] Patent Number: 5,840,015
[45] Date of Patent: Nov. 24, 1998

[54] APPARATUS FOR CONTROLLING A SUCTION PASSAGE IN AN ENDOSCOPE

[75] Inventor: Takayuki Ogino, Tokyo, Japan

[73] Assignee: Asahi Kagaku Kogyo Kabushiki Kaisha, Tokyo, Japan

[21] Appl. No.: 615,890

[22] Filed: Mar. 14, 1996

[30]         Foreign Application Priority Data

Mar. 17, 1995   [JP]   Japan ................................... 7-058509

[51] Int. Cl.⁶ ........................................................ A61B 1/12
[52] U.S. Cl. ........................... 600/159; 600/153; 600/156
[58] Field of Search ..................................... 600/153, 154, 600/155, 156, 158, 159; 251/142, 149, 149.6, 321, 325; 604/30, 33, 35, 246, 249, 118, 119, 121, 902

[56]              References Cited

U.S. PATENT DOCUMENTS

| 4,412,531 | 11/1983 | Chikashige . |
| 4,800,869 | 1/1989 | Nakajima ............................. 600/159 X |
| 5,057,080 | 10/1991 | Takahashi . |
| 5,226,885 | 7/1993 | Takahashi . |
| 5,301,656 | 4/1994 | Negoro et al. ....................... 600/159 X |
| 5,347,992 | 9/1994 | Pearlman et al. .................... 600/159 X |

FOREIGN PATENT DOCUMENTS 63-286129   11/1988   Japan .

Primary Examiner—Beverly M. Flanagan
Attorney, Agent, or Firm—Greenblum & Bernstein P.L.C.

[57]              ABSTRACT

An apparatus for controlling a suction passage in an endoscope includes a cylinder connected between an insertion pipe, on an insertion side of the endoscope, and a suction pipe, on a suction side of the endoscope. A piston is provided in the cylinder to move in an axial direction thereof to selectively connect or disconnect the insertion and suction pipes. The suction pipe, attached to the cylinder, is open at a position opposed to an outer periphery of the piston. A communication passage, provided in the piston, connects the insertion and suction pipes when the piston is in an operative position. An opening in the communication passage at the outer periphery of the piston is surrounded by an annular seal member to establish a water-tight connection between the open end of the communication passage and an open end of the suction pipe.

8 Claims, 4 Drawing Sheets

APPARATUS FOR CONTROLLING A SUCTION PASSAGE IN AN ENDOSCOPE

BACKGROUND OF THE INVENTION

1. Field of the Invention

The present invention relates to an apparatus for controlling a suction passage in an endoscope.

2. Description of Related Art

In a known suction passage controlling apparatus in an endoscope, a cylinder and a piston are provided. The piston is slidably fitted in the cylinder to move in the axial direction to open and close a suction passage. When the piston is in an inoperative position (standby position), external air is introduced into a suction device. When the piston is in an operative position, the suction device is functionally connected to a suction port formed at a front end of an insertion portion of the endoscope, so as to perform a sucking operation through the suction port.

In such a known suction passage controlling apparatus, the cylinder is provided with a connection hole to which an opening end of the suction passage, connected to the suction device, can be connected. The piston is provided with a communication hole, connected to the connection hole of the cylinder, to connect the suction port to the suction device when in the operative position, and a shut-off portion, which connects the connection hole the cylinder to the atmosphere (outside air), to disconnect the suction device from the suction port when in the inoperative position.

The piston is additionally provided on an outer peripheral surface thereof with peripheral grooves, in which sealing O-rings, each having a center coaxial to the axis of the piston, are fitted. The O-rings are axially spaced so that the communication hole is connected to the connection hole in a water-tight fashion when the piston is moved to the operative position, and the communication hole is disconnected from the connection hole when the piston is moved to the inoperative position.

In the known apparatus mentioned above, since the O-rings, fitted in the peripheral grooves of the piston, are axially spaced, dirt passing through the communication hole passes not only to the connection hole but also to the outer peripheral surface of the piston between the O-rings. Consequently, the outer peripheral portion of the piston to be sealed around the communication holes and the O-rings provided on the piston can be easily soiled or polluted. Since the O-rings are fitted in the peripheral grooves of the piston, it is difficult to clean or wash the O-rings, thus making the cleaning operation of the endoscope troublesome and time consuming.

SUMMARY OF THE INVENTION

It is an object of the present invention to provide a suction passage controlling apparatus in an endoscope in which no or little seal portion of a communication hole, formed on an outer peripheral surface of a piston, tends to be soiled or polluted, and the endoscope can be easily cleaned or washed.

To achieve the object mentioned above, according to an aspect of the present invention, there is provided an apparatus for controlling a suction passage in an endoscope comprising a cylinder connected between an insertion pipe, on an insertion side of the endoscope, and a suction pipe, on a suction side of the endoscope. A piston is provided in the cylinder to move in an axial direction thereof to selectively connect or disconnect the insertion and suction pipes. The suction pipe has an open end at a position opposed to an outer periphery of the piston. A communication passage is provided in the piston to connect the insertion and suction pipes when the piston is in an operative position. The communication passage has an open end at the outer periphery of the piston. An annular seal member is provided on the piston to surround the open end of the communication passage to establish a water-tight connection between the open end of the communication passage and an open end of the suction pipe.

Preferably, in the vicinity of the open end of the communication passage, the piston is provided with a large diameter portion to which the annular seal member is fitted.

It is preferred that the open end of the communication passage and the open end of the suction pipe have a substantially identical inner diameter, the thickness and the diameter of the annular seal member are such that when the annular seal member is fitted in the large diameter portion, the inner diameter of the annular seal member is substantially identical to the inner diameter of the open end of the suction pipe so as to form a smooth passage having a substantially uniform diameter, defined by the communication passage and the suction pipe.

The piston is provided with a peripheral groove which is axially spaced from the open end of the communication passage. In addition, the piston is provided with a further passage which connects the suction pipe to the atmosphere (outside air) through the peripheral groove, when the piston is in an inoperative position. This further passage comprises an axially elongated connecting groove and an elongated hole connected thereto.

Preferably, the center axis of the annular seal member is normal to an axis of the piston.

According to another aspect of the present invention, an apparatus for controlling a suction passage in an endoscope comprises a controlling unit provided between an insertion portion of the endoscope and a suction device. The controlling unit comprises a cylinder and a movable piston which is slidably provided in the cylinder to selectively move between an operative position, in which the insertion portion is connected to the suction device, and an inoperative position, in which the insertion portion is disconnected from the suction device. A communication passage is provided in the piston to connect the insertion portion and the suction device when the piston is in the operative position. The communication passage has an open end at the outer periphery of the piston. An annular seal member is secured to the piston to surround the open end of the communication passage and is elastically brought into contact with an inner peripheral surface of the cylinder.

Preferably, the piston is provided with a large diameter portion which surrounds the open end, so that the annular seal member is fitted in the large diameter portion to elastically abut, at one end surface thereof, against the inner peripheral surface of the cylinder.

The present disclosure relates to subject matter contained in Japanese Patent Application No. 7-58509 (filed on Mar. 17, 1995) which is expressly incorporated herein by reference in its entirety.

BRIEF DESCRIPTION OF THE DRAWINGS

The invention will be discussed below in detail with reference to the accompanying drawings in which.

DESCRIPTION OF THE PREFERRED EMBODIMENT

An embodiment of the present invention applied to a suction passage controlling apparatus in an endoscope will now be discussed below.

Figure 2:
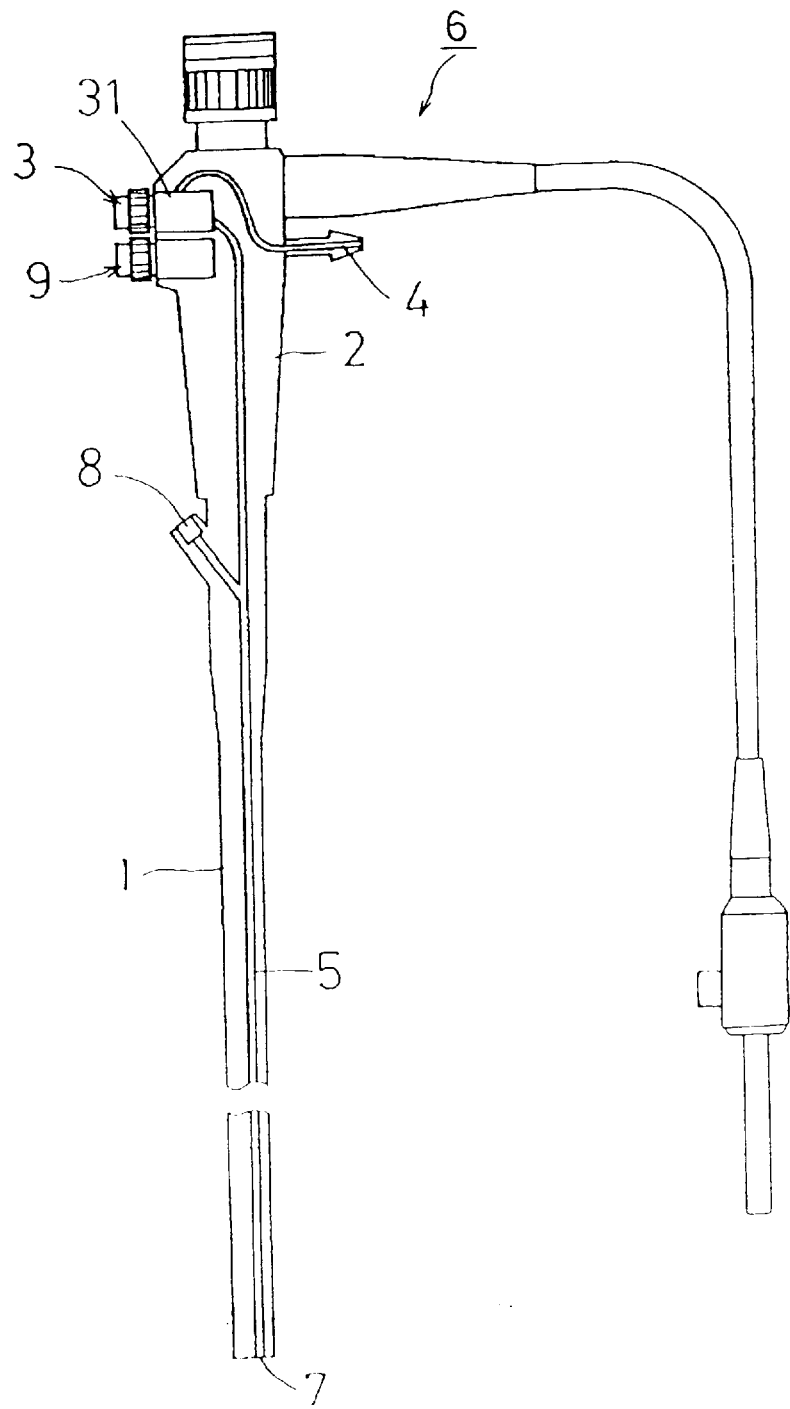
FIG. 2 is a side elevational view of the endoscope shown in FIG. 1.

As can be seen in FIG. 2, an endoscope 6 is comprised of an insertion portion 1 which is covered by a flexible tube and which can be inserted into a body cavity. A manipulating portion 2 is provided at a base end of the insertion portion 1, and a suction passage controlling apparatus 3 is provided on an upper portion of the manipulating portion 2.

The suction passage controlling apparatus 3 is provided with a cylinder 31 positioned between a suction pipe 4 and an insertion pipe 5. The suction pipe 4 (on the suction side, i.e., the left end as viewed in FIG. 2) is connected at one end thereof to the cylinder 31 and at the other end to an external suction device (not shown). The insertion pipe 5 is connected at one end thereof to the cylinder 31 and the other end opens into a front end of the insertion portion 1, as indicated by the numeral 7. The endoscope shown in FIG. 2 is provided with an insertion hole 8, in which forceps (not shown) can be inserted, and a water/air switching device 9 to respectively select a water or an air supply.

Figure 3:
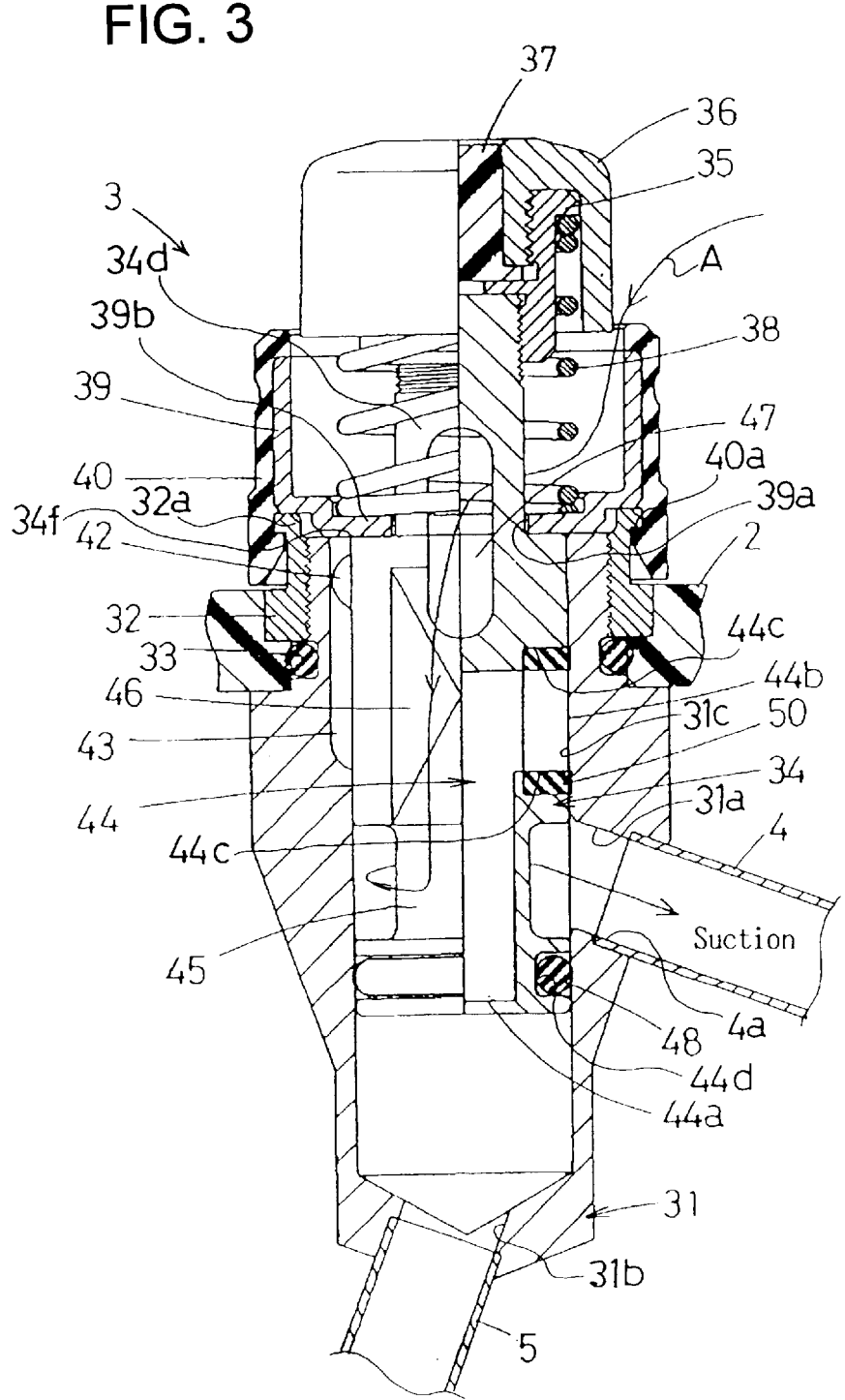
FIG. 3 is a longitudinal sectional view of a suction passage controlling apparatus in an endoscope in an inoperative position in which no sucking operation is carried out, according to the present invention; and, FIG. 4 is a side elevational view of a piston unit in a suction passage controlling apparatus according to the present invention.

FIG. 3 shows an enlarged view of the suction passage controlling apparatus 3. The cylinder 31 is provided and secured in the manipulating portion 2 by a nut 32, with the open end facing outward (upward in FIG. 3). Numeral 33 designates a sealing O-ring.

The cylinder 31 is provided on an outer peripheral surface thereof with a first connection hole 31a, in which one end of the suction pipe 4 is fitted, so as to connect the suction pipe 4 to the inside of the cylinder 31. On a lower end of the cylinder 31, a second connection hole 31b is provided in which one end of the insertion pipe 5 is fitted to connect the insertion pipe 5 to the inside of the cylinder 31.

A piston 34 is slidably fitted in the cylinder 31 to move in the axial direction thereof. The piston 34 is provided with a small diameter portion 34d which projects outward (upward in FIGS. 1 and 3) from the cylinder 31. Piston 34 is provided thereon with an operation button 36 attached thereto through a connection ring 35. The operation button 36 is provided at a center portion thereof with a marking shaft 37 which is made of, for example, a red plastic material. The outer end of the marking shaft 37 is visible from outside the endoscope.

Both the piston 34 and the operation button 36 are biased upward (in FIG. 1) by a compression coil spring 38. A cylindrical receptacle 39 secured to the cylinder 31 to receive the base end of the coil spring 38 is provided with an inner flange 39b having a central axial hole 39a in which the small diameter portion 34d of the piston 34 extends. A shoulder portion 34f of the piston 34, connected to the small diameter portion 34d, abuts against the inner flange 39b of the cylindrical receptacle 39 to restrict the axial movement of the piston 34. Namely, the cylindrical receptacle 39 serves as a stopper to prevent the piston 34 from moving out of the cylinder 31 beyond a predetermined axial position.

A securing rubber ring 40 with which the cylindrical receptacle 39 is integrally covered is provided on a lower end thereof with an inner flange 40a which is engaged by an end projection 32a provided on the nut 32. Consequently, an assembly (piston unit) of the piston 34 and the operation button 36 is connected to the cylinder 31.

Figure 4:
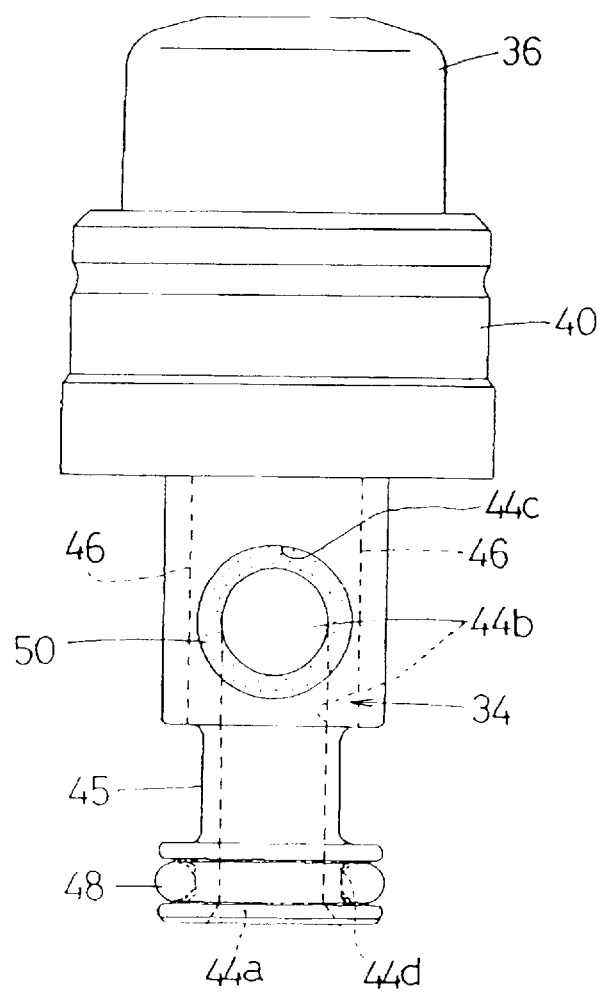

When the securing rubber ring 40 is disengaged from the nut 32, by elastically deforming the securing rubber ring 40, the piston 34 can be removed from the cylinder 31 as shown in FIG. 4. The piston 34 is provided with a pin 42 which projects from an outer peripheral surface thereof. The cylinder 31 is provided with an axial (or longitudinal) groove 43 formed on an inner surface thereof, so that the pin 42 is slidably fitted in the axial groove 43 to prevent the piston 34 from rotating relative to the cylinder 31.

Figure 1:
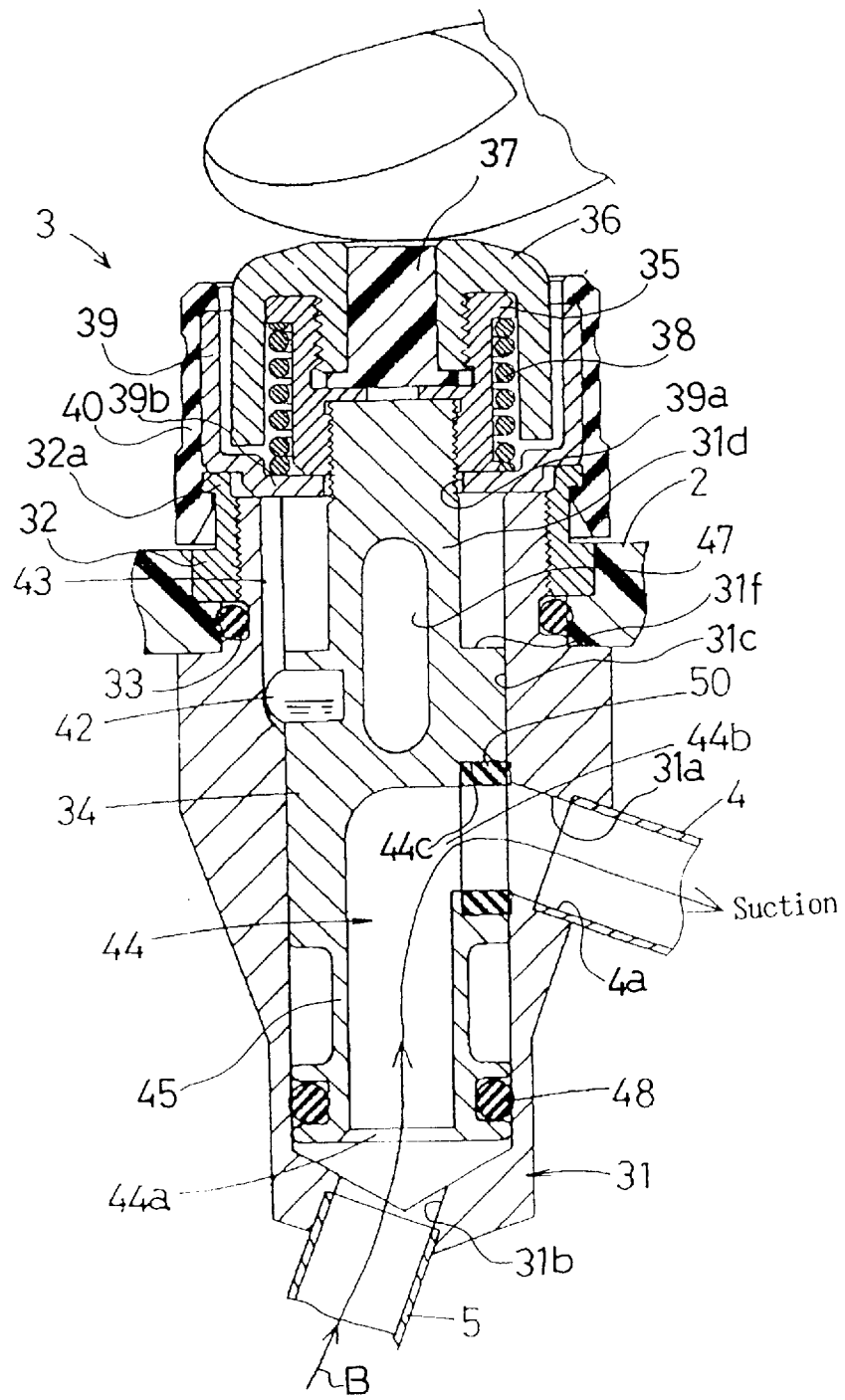
FIG. 1 is a longitudinal sectional view of a suction passage controlling apparatus in an endoscope in an operative position in which the sucking operation is carried out, according to the present invention.

The portion of the piston 34 that is located within the cylinder 31 is provided with a communication hole 44 which opens into the lower end of the piston 34, as indicated by 44a in FIG. 1. The other open end 44b of the communication hole 44 opens into the outer peripheral surface of the piston 34 to be substantially perpendicular to the axis of the piston 34 (cylinder 31). In the operative position shown in FIG. 1, in which the piston 34 is depressed into the cylinder 31, the open end 44b of the communication hole 44 is opposed to the connection hole 31a of the cylinder 31 in which one end of the suction pipe 4 is inserted. The open end 44b, the connection hole 31a, and an open end 4a have substantially identical inner diameters.

The open end 44b is provided, on the portion thereof connected to the connection hole 31a, with a large diameter portion 44c in which an annular seal member (resilient sealing member) 50 is fitted. The annular seal member 50 can be made from an elastically deformable material such as rubber. Note that a center axis of the annular seal member 50 is normal to an axis of the piston 34. The diameter of the large diameter portion 44c is larger than the inner diameter of the connection hole 31a (or the open end 4a or the communication hole 44) by a value corresponding to the thickness of the annular seal member 50, so that when the annular seal member 50 is fitted in the large diameter portion 44c, the inner diameter of the annular seal member 50 is substantially identical to the connection hole 31a.

In other words, the diameter and thickness of the annular seal member 50 are selected such that when the annular seal member 50 is appropriately fitted in the large diameter portion 44c, the inner diameter of the annular seal member 50 is substantially identical to the inner diameter of the connection hole 31a (or the open end 44a or the communication hole 44). Moreover, when the annular seal member 50 is fitted in the large diameter portion 44c to surround the open end 44b, the annular seal member 50 is elastically pressed against the inner peripheral surface 31c of the cylinder 31. Namely, the annular seal member 50 projects slightly in the radial direction of the piston 34 from the outer peripheral surface of the piston 34 when the annular seal member 50 is fitted in the large diameter portion 44c, in a free state (i.e., before the piston 34 is fitted in the cylinder 31).

Dirt can smoothly pass and be sucked through a passage of uniform diameter (having no stepped portion), defined by the open end 44b, the annular seal member 50, the connection hole 31a, and the open end 44a, etc. Consequently, no or little dirt accumulates on the inner peripheral surface of the annular seal member 50 or the outer surface of the piston 34, or the inner surfaces of the cylinder 31, or other seal members, such as an O-ring 48, etc.

As can be clearly seen in FIG. 4, the piston 34 is provided with a peripheral groove 45 directly below the open end 44b, and a lower peripheral groove 44d directly below the peripheral groove 45. The O-ring 48, made of a resilient material such as rubber, is fitted in the peripheral groove 44d. The piston 34 is provided with a connecting radial longitudinal groove 46 which extends in a direction parallel to the axis of the piston 34 and is connected to the peripheral groove 45. The piston 34 is also provided with an axially elongated hole 47 which is connected to the groove 46. The upper end of the elongated hole 47 extends into the cylindrical receptacle 39, when the piston 34 is in the inoperative position and connects the elongated hole 47 to the atmosphere (outside air).

In the inoperative position shown in FIG. 3, in which the piston 34 is not moved (completely) into the cylinder 31, the open end 44b is opposed to a portion of the inner peripheral surface 31c of the cylinder 31 that is located above the connection hole 31a (connected to the suction pipe 4), and the peripheral groove 45 is opposed to the connection hole 31a of the cylinder. Consequently, in the inoperative position, air is introduced into the suction pipe 4 through the elongated hole 47, the connecting grooves 46 and the peripheral groove 45, as indicated by arrow "A" in FIG. 3. Also, in this state, the annular seal member 50, fitted in the large diameter portion 44c, comes into close contact with the inner peripheral surface 31c of the cylinder 31. Hence, the open end 44b is isolated from the atmosphere or the suction device (not shown). The suction pipe 4 and the insertion pipe 5 are sealed and disconnected by the annular seal member 50 and the O-ring 48 provided at the lower end of the piston 34. Thus, no suction force is produced in the insertion pipe 5 extending into the insertion portion 1.

In the inoperative position shown in FIG. 3, if the operation button 36 is depressed by an operator's finger to move the piston 36 downwardly, the open end 44b of the piston 34 is aligned with the connection hole 31a (suction pipe 4) of the cylinder, so that the suction pipe 4 and the insertion pipe 5 are connected through the communication hole 44 to carry out the sucking operation through the front end 7 (FIG. 2), as indicated by arrow "B" in FIG. 1. During the movement of the piston 34, the periphery of the front open end 44a of the piston 34 is sealed by the O-ring 48, and the periphery of the open end 44b of the piston 34 is sealed by the annular seal member 50. Consequently, no suction of air into the suction pipe 4 through the peripheral portion of the piston 34 occurs during the movement of the piston.

When the endoscope is not in use, the securing ring 40 is disengaged from the nut 32, so that the piston 34 and the operation button 36, etc., can be detached as a single unit from the cylinder 31, as shown in FIG. 4. Consequently, the annular seal member 50 is exposed to the outside from the outer peripheral surface of the piston 34 and can thus be easily cleaned and washed.

What is claimed is:

1. An endoscope with an apparatus for controlling a suction passage in the endoscope, comprising:
   a cylinder connected between an insertion pipe, on an insertion side of said endoscope, and a suction pipe, on a suction side of said endoscope;
   a piston provided in said cylinder to move in an axial direction thereof to selectively connect or disconnect said insertion pipe and said suction pipe, said suction pipe and said cylinder having mating open ends at a position opposed to an outer periphery of said piston;
   a communication passage provided in said piston to connect said insertion pipe and said suction pipe when said piston is in an operative position, said communication passage having an open end at said outer periphery of said piston; and
   an annular seal member provided on said piston to surround said open end of said communication passage to establish a water-tight connection between said open end of said communication passage and said end of said suction pipe, a central axis of said annular seal being normal to a central axis of said piston.

2. The endoscope with the suction passage controlling apparatus according to claim 1, wherein said piston is provided with a large diameter portion in a vicinity of said open end of said communication passage, said annular seal member being fitted in said large diameter portion.

3. The endoscope with the suction passage controlling apparatus according to claim 2, wherein said open end of said communication passage and said open end of said suction pipe have substantially identical inner diameter, and wherein a thickness and a diameters, of said annular seal member are such that when said annular seal member is fitted in said large diameter portion, an inner diameter of said annular seal member is substantially identical to said inner diameter of said open end of said suction pipe to form a smooth passage having a substantially uniform diameter, defined by said communication passage and said suction pipe.

4. The endoscope with the suction passage controlling apparatus according to claim 1, wherein said piston is provided with a peripheral groove axially spaced from said open end of said communication passage.

5. The endoscope with the suction passage controlling apparatus according to claim 4, wherein said piston is provided with a further passage which connects said suction pipe to an external atmosphere through said peripheral groove when said piston is in an inoperative position.

6. The endoscope with the suction passage controlling apparatus according to claim 5, wherein said further passage comprises an axially elongated connecting groove and an elongated hole connected thereto.

7. An endoscope with an apparatus for controlling a suction passage in the endoscope, comprising:
   a controlling unit provided between an insertion portion of said endoscope and a suction device, said controlling unit comprising a cylinder and a movable piston slidably provided in said cylinder to selectively move between an operative position, at which said insertion portion is connected to said suction device, and an inoperative position, at which said insertion portion is disconnected from said suction device;
   a communication passage provided on said piston to connect said insertion portion and said suction device when said position is at said operative position, said communication passage having an open end at an outer periphery of said piston; and
   an annular seal member secured to said piston to surround said open end of said communication passage and which is elastically brought into contact with an inner peripheral surface of said cylinder, a central axis of said piston being perpendicular to a central axis of said annular seal.

8. The endoscope with the suction passage controlling apparatus according to claim 7, wherein said piston is provided with a large diameter portion which surrounds said open end, so that said annular seal member is fitted in said large diameter portion to elastically abut, at an end surface thereof, against an inner peripheral surface of said cylinder.

* * * * *

UNITED STATES PATENT AND TRADEMARK OFFICE
CERTIFICATE OF CORRECTION

PATENT NO. : 5,840,015
DATED : November 24, 1998
INVENTOR(S) : Takauuki OGINO

It is certified that error appears in the above-identified patent and that said Letters Patent is hereby corrected as shown below:

On cover page, at item [73], Assignee, "Kagaku" should be —Kogaku—.

At column 6, line 19 (claim 3, line 4) of the printed patent, "diameter" should be —diameters.—

At column 6, line 20 (claim 3, line 5) of the printed patent, "diameters" should be —diameter—.

Signed and Sealed this

Twenty-ninth Day of February, 2000

Attest:

Q. TODD DICKINSON

Attesting Officer

Commissioner of Patents and Trademarks